United States Patent
Sokolov et al.

(10) Patent No.: US 12,168,794 B2
(45) Date of Patent: Dec. 17, 2024

(54) METHODS FOR IMMUNOASSAYS USING ELECTROCHEMICAL MEASUREMENT

(71) Applicant: OSLER DIAGNOSTICS LIMITED, Oxford (GB)

(72) Inventors: Stanislav Sokolov, Oxford (GB); James Merotra, Oxford (GB); Konstantinos Psarros, Oxford (GB); Samuel Whitby, Oxford (GB); Adriano Dos Santos, Oxford (GB); Flavio Cesar Bedatty Fernandes, Oxford (GB)

(73) Assignee: Osler Diagnostics Limited, Oxford (GB)

( * ) Notice: Subject to any disclaimer, the term of this patent is extended or adjusted under 35 U.S.C. 154(b) by 771 days.

(21) Appl. No.: 17/281,063

(22) PCT Filed: Oct. 2, 2019

(86) PCT No.: PCT/GB2019/052769
§ 371 (c)(1),
(2) Date: Mar. 29, 2021

(87) PCT Pub. No.: WO2020/070486
PCT Pub. Date: Apr. 9, 2020

(65) Prior Publication Data
US 2021/0332405 A1    Oct. 28, 2021

(30) Foreign Application Priority Data
Oct. 2, 2018  (GB) .................................. 1816103

(51) Int. Cl.
*G01N 27/327*   (2006.01)
*C12Q 1/00*   (2006.01)
*C12Q 1/28*   (2006.01)

(52) U.S. Cl.
CPC ............... *C12Q 1/005* (2013.01); *C12Q 1/28* (2013.01); *G01N 2333/4737* (2013.01)

(58) Field of Classification Search
CPC .. C12Q 1/005; C12Q 1/28; G01N 2333/4737; G01N 27/327; G01N 27/02; G01N 27/026
See application file for complete search history.

(56) References Cited

U.S. PATENT DOCUMENTS 5,210,015 A * 5/1993 Gelfand ............... C12Q 1/6818
436/63
5,418,136 A * 5/1995 Miller ............. G01N 33/54373
436/805

(Continued)

FOREIGN PATENT DOCUMENTS

CN    105092832    11/2015
CN    106771112    5/2017

(Continued)

OTHER PUBLICATIONS

Lin et al., "Electrochemical Immunosensor Based on Polycalconcarboxylic Acid Modified Electrode for the Determination of Alpha-Fetoprotein," Journal of Electrochemistry, vol. 18, issue 4 (Special Issue of Chemical power sources), pp. 371-376 (Year: 2012).*

(Continued)

*Primary Examiner* — Alexander S Noguerola
(74) *Attorney, Agent, or Firm* — KNOBBE, MARTENS, OLSON & BEAR LLP (57) ABSTRACT

Disclosed herein is a method for detecting a binding event between an immobilised primary antibody and a target analyte-secondary antibody-enzyme complex using an electrochemical measurement technique.

18 Claims, 6 Drawing Sheets

(56) References Cited

U.S. PATENT DOCUMENTS

| | | | |
|---|---|---|---|
| 5,688,642 A * | 11/1997 | Chrisey | B82Y 5/00 |
| | | | 435/5 |
| 6,391,558 B1 | 5/2002 | Henkens et al. | |
| 6,723,524 B1 | 4/2004 | Hermens et al. | |
| 7,659,089 B2 | 2/2010 | Hasenbank et al. | |
| 10,753,940 B2 | 8/2020 | Ingber et al. | |
| 10,908,154 B2 | 2/2021 | Hu et al. | |
| 2004/0142405 A1 | 7/2004 | Alfonta et al. | |
| 2004/0214253 A1* | 10/2004 | Paek | G01N 33/558 |
| | | | 435/7.92 |
| 2005/0136500 A1 | 6/2005 | Yang et al. | |
| 2006/0154320 A1 | 7/2006 | Zuk et al. | |
| 2006/0160100 A1 | 7/2006 | Gao et al. | |
| 2007/0231794 A1 | 10/2007 | Dill et al. | |
| 2011/0053289 A1 | 3/2011 | Lowe et al. | |
| 2013/0115619 A1 | 5/2013 | Clark | |
| 2013/0189680 A1* | 7/2013 | May | G01N 1/30 |
| | | | 435/7.9 |
| 2017/0153233 A1 | 6/2017 | Gurgo et al. | |
| 2017/0285021 A1 | 10/2017 | Ying | |
| 2018/0164303 A1 | 6/2018 | Hu et al. | |

FOREIGN PATENT DOCUMENTS

| | | |
|---|---|---|
| CN | 111044724 | 4/2020 |
| CN | 111610324 | 9/2020 |
| EP | 0038181 | 10/1981 |
| EP | 3023789 | 5/2016 |
| FR | 2963107 | 1/2012 |
| JP | 2014-206391 | 11/2017 |
| WO | WO 2000/047983 | 8/2000 |
| WO | 2004010103 A2 | 1/2004 |
| WO | WO 2004/071641 | 8/2004 |
| WO | WO 2008/057366 | 5/2008 |
| WO | WO 2011/057347 | 5/2011 |
| WO | WO 2012/010654 | 1/2012 |
| WO | WO 2017/024044 | 2/2017 |
| WO | WO 2017/132564 | 8/2017 |
| WO | WO 2018/140540 | 8/2018 |
| WO | WO 2019/023567 | 1/2019 |
| WO | WO 2020/099886 | 5/2020 |
| WO | WO 2020/120990 | 6/2020 |
| WO | WO 2020/142313 | 7/2020 |

OTHER PUBLICATIONS

Wang et al., "Ultrasensitive Label-free Electrochemical Immunosensor based on Multifucitionalized Graphene Nanocomposites for the detection of Alpha Fetoprotein," Scientific Reports | 7:42361 | DOI: 10.1038/srep42361 (Year: 2017).*

Sharma et al., Label-free electrochemical impedance biosensor to detect human interleukin-8 in serum with sub-pg/ml sensitivity, Biosensors and Bioelectronics 80 (2016) 607-613 (Year: 2016).*

6. Ahirwal et al., "Gold nanoparticles based on sandwich electrochemical immunosensor," Biosensors and Bioelectronics 25 (2010) 2016-2020 (Year: 2010).*

Akter et al., Amplified Elect4rochemcial Detection of a Cancer Biomarker by Enhanced Precipitation Using Horseradish Peroxidase Attached on Carbon Nanotubes, Anal. Chem. 2012, 84, 6407-6415 (Year: 2012).*

Ding et al., "Nanogold-functionalized g-C3N4 nanohybrids for sensitive impedimetric immunoassay of prostate-specific antigen using enzymatic biocatalytic precipitation," Biosensors and Bioelectronics 85 (2016) 212-219 (Year: 2016).*

Esteban-Fernández de Ávila et al., "Lipoprotein(a) determinant in human serum using a nitrilotriacetic acid derivative immunosensing scaffold on disposable electrodes," Anal Bioanal Chem (2014) 406:5379-5387 (Year: 2014).*

Esteban-Fernández de Ávila et al., "Ultrasensitive amperometric magnetoimmunosensor or human C-reactive protein quantification in serum," Sensors and Actuators B 188 (2013) 212-220 (Year: 2013).*

Esteban-Fernández de Ávila et al., "Multiplexed Determination of Amino-Terminal Pro-B-Type Natriuretic Peptide and C-Reactive Protein Cardiac Biomarkers in Human Serum at a Disposable electrochemical Magnetoimmunosensor," Electroanalysis 2014, 26, 254-261 (Year: 2014).*

Ramachandran et al., "Long-term dry storage of an enzyme-based reagent system for ELISA in point-of-care devices," Analyst Mar. 21, 2014; 139(6): 1456-1462. doi:10.1039/c3an02296j (Year: 2014).*

Vector Laboratories product literature for ImmPRESS™ Excel Staining Kit (Year: 2016).*

USPTO human translation of Lin et al., "A Study of Alpha-Fetoprotein Electrochemical Immunosensor Based on Novel Polycalconcarboxylic Acid Modified Electrode," Journal of Electrochemistry, vol. 18, issue 4 (Special Issue of Chemical power sources), pp. 371-376 (Year: 2012).*

International Search Report and Written Opinion for PCT Appl. No. PCT/GB2019/052769, mail date Jan. 8, 2020, 10 Pages.

Xiaohui, Geng, et al., "Sensitive Impedimetric Immunoassay of Japanese Encephalitis Virus Based on Enzyme Biocatalyzed Precipitation on a Gold Nanoparticle-modified Screen-printed Carbon Electrode.", Analytical Sciences, Oct. 1, 2016. pp. 1105-1109.

Xiaobo, Yu et al., "An Impedance Array Biosensor for Detection of Multiple Antibody-antigen Interactions", The Analyst, vol. 131, No. 6, Jan. 1, 2006. pp. 745-750.

Tang, et al., "Enzymatically Biocatalytic Precipitates Amplified Antibody-antigen Interaction for Super Low Level Immunoassay: An Investigation Combined Surface Plasmon Resonance With Electrochemistry", Biosensors and Bioelectronics, vol. 21, No. 5, Nov. 15, 2007. pp. 668-674.

Ding, Li-Li, et al., "Nanogold-functionalized g-C3N4 Nanohybrids for Sensitive Impedimetric Immunoassay of Prostate-specific Antigen Using Enzymatic Biocatalytic Precipitation", Biosensors and Bioelectronics, vol. 85, May 6, 2016. pp. 212-219.

Search Report for Great Britain Patent Appl. No. 1816103.4, mail date May 30, 2019, 7 Pages.

Yu, Xiaobo, et al. "An Impedance Biosensor Array for Label-free Detection of Multiple Antigen-antibody Reactions," Frontiers in Bioscience 11, 983-990, 2006.

Li, Jing, et al. "Carbon Nanotubes Labeled with Aptamer and Horseradish Peroxidase as a Probe for Highly Sensitive Protein Biosensing by Postelectropolymerization of Insoluble Precipitates on Electrodes," American Chemical Society, Issue 15, vol. 87, pp. 7610-7617. (2015).

Ruan, Chuanmin, et al. "Immunobiosensor Chips for Detection of *Escherichia coli* O157:H7 Using Electrochemical Impedance Spectroscopy," Analytical Chemistry, vol. 74, No. 18, pp. 4814-4820, (2002).

Gehring AG et al (1996) Journal of Immunological Methods, vol. 195(1), p. 15-25.

Montiel VRS et al (2015) Talanta vol. 131, p. 156-162.

Montiel VRS et al (2016) Sensors and Actuators B: Chemical, vol. 236 p. 825-833.

Thio Tzer Hwai Gilbert et al, (2015) PLOS ONE, vol. 10, No. 4, p. e0121836.

Zhang C et al (2022) Talanta vol. 240, e123173.

\* cited by examiner

Figure 1

DAB

TMB

METHODS FOR IMMUNOASSAYS USING ELECTROCHEMICAL MEASUREMENT

RELATED APPLICATIONS

This application is a national phase application filed under 35 USC § 371 of PCT Application No. PCT/GB2019/052769 with an International filing date of Oct. 2, 2019, which claims priority of GB Patent Application 1816103.4 filed Oct. 2, 2018. Each of these applications is herein incorporated by reference in its entirety for all purposes.

BACKGROUND TO THE INVENTION

The present application relates to a method for measuring the level of an analyte in a sample using electrochemical measurement techniques, including impedance assays, and in particular to a method for determining the presence or amount of an analyte in a sample using direct impedance measurement.

Immunoassays are often used for the detection of a specific analyte within a sample. For example, pairs of antibodies that can bind to an analyte to form a sandwich that is detectable by means of an enzyme or particulate label on one of the antibodies are well known and available for a wide range of different analytes of interest. For example, antibodies to a particular biomarker, such as testosterone or cortisol, may be used to test levels of these substances in the saliva, blood or urine samples.

The presence of the antibody-analyte sandwich can be detected by various means including by the use of impedance measurements. There have also been some reports of assays that utilise an enzyme substrate to amplify the assay signal, and thus improve assay sensitivity, by generating an insoluble precipitate that increases impedance. However, to date, these reports relate to laboratory methods that aren't necessarily suitable for use in commercial in-vitro diagnostic assay methods or devices.

Yu et al 2006 (see reference 1) describes an electrochemical immunoassay that uses AEC to generate an insoluble precipitate for the detection of HBsAg using an enzyme labelled antibody. The assay utilises a redox probe and faradaic impedance measurement to detect and quantify the target analyte. Yu et al. utilised a self assembled monolayer, a molecular layer requiring long preparation times (16 hours) and is unstable due to oxidation of the thiol groups.

For example, Li et al. (see reference 2) discloses a laboratory method that uses carbon nanotubes (CNTs) labelled with aptamer and horseradish peroxidase (HRP) as a probe to amplify the impedimetric sensing of aptamer-protein (thrombin as model) interaction. However, the method disclosed relies on the use of an active electropolymerization step in order to increase the amount of insoluble precipitates (DAB) produced and thus provide sufficient signal amplification for analyte detection. In addition, the assay uses oligonucleotide aptamers and carbon nanotubes and, therefore, the methodology described is not readily adaptable for the assay of a range of different analytes, or for use in a device that can be manufactured at high volume and low cost. It appears that this assay method is prone to non-specific binding.

Many assays for biomolecules, including viruses, have been carried out on electrode devices, for example Geng et al 2016 (see reference 3). However, these methods all rely on sandwich assembly on a surface involving repeated steps of washing and changes of reagents, first with the target sample containing the biomolecule/virus, then washing, then exposure to a secondary antibody, then washing again before the actual assay is performed. Thus the test takes many cycles of reagent exchange and many hours to set up in order to complete. Such assembly methods are not suitable for commercial in-vitro diagnostic assay methods or devices where the sample is applied and a reading taken.

Therefore, there is a requirement and a need in the technical field of fast and efficient diagnostic assays to develop a simple, robust and sensitive electrochemical measurement immunoassay method that can be used to accurately detect and/or quantify a wide range of target analytes. It is against this background that the present invention has arisen.

SUMMARY OF THE INVENTION

The methods as described herein utilise electrochemical measurement to detect and/or quantify the presence of a target analyte via immobilisation to an electrode. These measurements are thus a measurement of the electrical signal change across an electrode generated by the formation of the sandwich complex on the electrode surface and the generation of the insoluble precipitate produced on the surface of the electrode by the action of the captured enzyme label when contacted with a suitable enzyme substrate. The methods described herein utilise electrochemical measurement, for example faradaic impedance measurement or non-faradaic impedance measurement and thus use AC current and may, therefore, be practiced without the use of a redox probe reagent.

The methods described herein may comprise a single incubation step to form the enzyme labelled antibody sandwich by contacting the immobilised antibody with an assay mixture comprising the test sample, secondary antibody and enzyme label reagents. This may be advantageous to reduce overall assay time, simplify assay design and/or ensure the detection of very low concentration analytes.

However, additional steps are required to optimise a single step incubation assay compared to a traditional multi-step assay. Designing a three-component assay system (antigen, secondary antibody and enzyme) is an intrinsically more complex process and therefore requires additional screening tests to detect non-specific interactions (higher background) or steric hindrance effects (slower reaction kinetics). For example, to select a polymerized form of horseradish peroxidase (HRP) enzyme to use in an assay system it is necessary to screen different polymer types and sizes for non-specific interactions with target antigen, secondary antibody, and functionalised sensor surface (primary antibody and blocking reagent).

The single incubation step has significant advantages over the traditional multi-step process. Firstly, by adding all the reagents together (antigen, secondary antibody, enzyme) there are less steps required in order to perform the sandwich immunoassay. This can save time from the incubation, reduce the washing steps and therefore improve reproducibility and reduce variation. In addition, for PoC (point of care) devices where reagent space is limited, by having all the components together can save precious space in a cartridge system and significantly simplifies workflow. This in turn, leads to reduced error from the system and further improving the reproducibility of the assay. Advantageously, the methods provided herein do not require electropolymerisation of the insoluble precipitate.

Advantageously, such a method may be performed on a single use assay cartridge, for example such as those described in U.S. Pat. No. 8,425,745. The devices can be configured to include all the reagents necessary for carrying out the method described herein so that the end user simply needs to add a test sample to the device.

Thus in a first aspect provided herein is a method for detecting a binding event between primary antibody-target analyte complex and a secondary antibody-enzyme complex using electrochemical impedance spectroscopy, the method comprising contacting an primary antibody immobilised on an electrode surface with a target analyte and a secondary antibody and enzyme label in one or more solutions to create a sandwich complex bound to the electrode surface, contacting the sandwich complex with a substrate for the enzyme, wherein the substrate is converted by the enzyme into an insoluble precipitate on the electrode surface; and measuring the impedance signal using electrochemical impedance spectroscopy before and during and/or after the formation of the insoluble precipitate on the electrode surface.

In a further aspect provided herein is a method for detecting a binding event between an immobilised primary antibody and a target analyte-secondary antibody-enzyme complex using an electrochemical measurement technique, the method comprising:
  incubating a target analyte, a secondary antibody and an enzyme label in a single solution;
  contacting a primary antibody immobilised on an electrode surface with the single solution of the target analyte, the secondary antibody and the enzyme label to create a sandwich complex bound to the electrode surface;
  contacting the sandwich complex with a substrate for the enzyme, wherein the substrate is converted by the enzyme into an insoluble precipitate on the electrode surface; and
  measuring an electrochemical signal during and/or after the formation of the insoluble precipitate on the electrode surface.

The binding event may be detected when the measured impedance during and/or after formation of the insoluble precipitate varies by more than 5% from the measured impedance before formation. In embodiments the method may be carried out such that the target analyte, secondary antibody and enzyme label are incubated in single solution for up to 5 mins before contacting the primary antibody.

The enzyme label may be selected from horseradish peroxidase (HRP), alkaline phosphatase (AP), glucose oxidase and β-galactosidase. The enzyme label may be in a polymeric form. Any suitable substrate may be used, for example DAB (3,3'-diaminobenzidine), metal-enhanced DAB, AEC (3-amino-9-ethylcarbazole), BCIP (5-bromo-4-chloro-3-indolyl phosphate), NBT (nitro-blue tetrazolium chloride), TMB (3,3',5,5'-tetramethylbenzidine), ELF (enzyme-labelled fluorescence) or OPD (o-phenylenediamine dihydrochloride). The substrate may be stabilised DAB, for example ImmPact™ DAB. The enzyme substrate may be TMB (tetramethylbenzidine), which can be used as a substrate without requiring a further redox probe and can therefore be directly measured in a buffered solution.

The primary antibody may be immobilised on the electrode surface by EDC/NHS (1-ethyl-3-(3-dimethylaminopropyl) carbodiimide/N-hydroxysuccinimide) activation, other linking chemistries (maleimide, click chemistry, epoxy, tosyl, chloromethyl, iodoacetamide), biotin-streptavidin or passive adsorption.

The electrochemical measurement technique can be electrochemical impedance spectroscopy, differential pulse voltammetry, square wave voltammetry, cyclic voltammetry, chronoamperometry, open circuit potential or chronopotentiometry.

The duration of electrochemical impedance measurement may be up to 5 minutes in duration. The duration of measurement may be for example 20 seconds to 5 minutes. The duration of electrochemical impedance measurement may be between 1 and 5 mins, 1 to 4 mins, 1 to 3 mins, 2 to 3 mins or, preferably, 1 to 2 mins.

The duration of the differential pulse voltammetry measurement can be between 30 seconds to 2 mins.

In embodiments the secondary antibody binds directly to the target analyte.

In embodiments the electrical impedance spectroscopy measurement comprises faradaic impedance measurement.

In embodiments the impedance signal is measured during the formation of the insoluble precipitate by the use of a one or more redox probes.

In embodiments the electrical impedance spectroscopy measurement uses the elapsed time from addition of the enzyme substrate until a threshold impedance value is reached at a characteristic frequency to quantify the binding event. The characteristic frequency may be determined using immittance function analysis.

In embodiments the electrical impedance spectroscopy measurement comprises measuring the reduction of oxygen generated by chronoamperometric measurement.

In some embodiments more than one redox probe is present for the impedance measurement.

In some embodiments the electrical impedance spectroscopy measurement comprises cyclic voltammetry.

In other embodiments the electrical impedance spectroscopy measurement is non-faradaic impedance measurement.

The electrode can be fabricated from a suitable material, for example gold or carbon.

The target molecule can be present in a sample obtained as whole blood, plasma or serum. The target molecule may be C-reactive protein (CRP) or troponin.

Disclosed herein is a method for detecting a binding event between an immobilised primary antibody and a CRP-secondary antibody-HRP complex using an electrochemical measurement technique, the method comprising:
  incubating a sample containing CRP, a secondary antibody and an enzyme label in a single solution;
  contacting a primary antibody immobilised on an electrode surface with the single solution of the target analyte, the secondary antibody and the enzyme label to create a sandwich complex bound to the electrode surface;
  contacting the sandwich complex with a substrate for the HRP, wherein the substrate is converted by the enzyme into an insoluble precipitate on the electrode surface; and
  measuring an electrochemical signal during and/or after the formation of the insoluble precipitate on the electrode surface.

DETAILED DESCRIPTION OF THE INVENTION

Immunoassays are often used for the detection of a specific analyte within a sample. Pairs of antibodies that can bind to an analyte to form a sandwich that is detectable by means of an enzyme or particulate label on one of the antibodies are well known and available for a wide range of different analytes of interest. These labels can be detected by various means such as fluorescent intensity or similar optical methods. In a sandwich assay the primary antibody is bound to a surface and the rest of the surface deactivated using blocking proteins. The antigen can then bind to the primary antibody and a secondary antibody is added which will bind to the primary-bound antigen. In practice the secondary antibody is modified by a label which can be detected by various means such as fluorescent intensity or similar optical methods.

An alternative method is to use electrochemical measurements, which are attractive as the sandwich can be detected directly on an electrode surface using a range of electrochemical measurements but are often limited by the necessary sensitivity amid a number of complex processes. The electrode surfaces can be for a single measurement or can allow multiple separate measurements to be performed independently using electrode arrays formed using standard thin film processing techniques.

One of the most sensitive electrochemical techniques is electrochemical impedance spectroscopy (EIS), which effectively separates a number of complex processes occurring at an electrochemical interface by measuring at a range of frequencies, thus separating processes by the characteristic timescales they occur on. In EIS, the parameters measured include various resistances and capacitances relating to the electrode and secondary processes. Of particular use to immunoassays, are the processes related to electron transfer at the modified electrode surface; an increase in bound species (such as antibodies) will affect these processes. The main surface specific parameters that can be measured are the charge transfer resistance (RCT) and the double layer capacitance (CDL), of which the RCT gives the most direct measurement of surface blocking. However, low concentrations of surface bound species will have a minimal effect on these.

Figure 1:
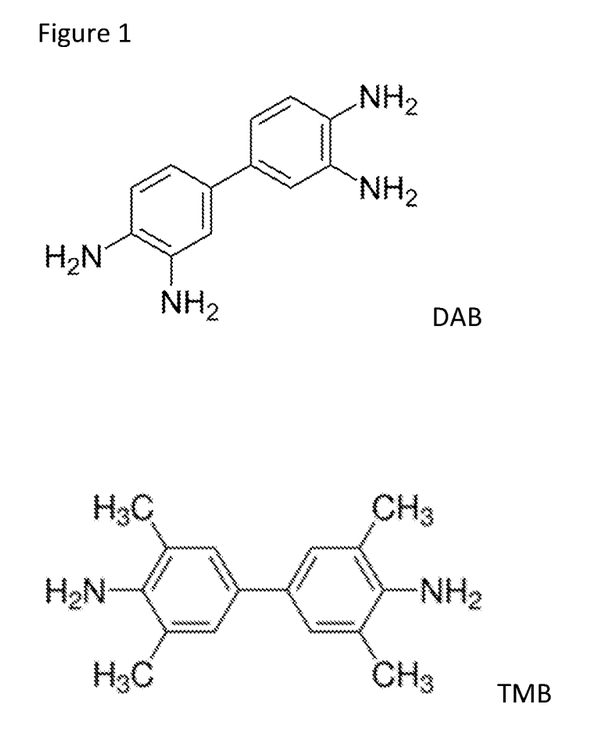
FIG. 1 shows the structure of 3,3'-Diaminobenzidine (DAB) and tetramethylbenzidine (TMB) according to the present invention.

In order to increase electrochemical sensitivity to access the physiological range required, amplification of the signal is required. Secondary antibodies can be modified with bulky molecules but this will only provide a small amplification. To address this 'enzyme boost' mechanisms can be used (see references 1-4). For this method, rather than modify the secondary antibody with an optical label, an enzymatic label can be used to act as a catalyst to further block the electrode surface and thus increase the electrochemical sensitivity. In the system described herein we use an enzymatic polymerisation catalyst; on addition of a monomer capable of enzyme-catalysed polymerisation to an insoluble (precipitating) product, a blocking layer can be readily and controllably formed and thus amplify the electrochemical signal in EIS. In this assay the polymerisation of 3,3'-Diaminobenzidine (DAB) (see FIG. 1) occurs via oxidation using hydrogen peroxide catalysed by the horseradish peroxidase (HRP) enzyme.

Other enzymes that are routinely used to label antibodies are known in the art, including alkaline phosphatase, glucose oxidase and β-galactosidase, and may be used in the methods described herein when combined with an appropriate substrate, i.e. one that forms an insoluble precipitate in the presence of the enzyme and, therefore, amplifies the impedance signal.

Precipitating substrates that may be used in the assay methods described herein are set out in the table below. Precipitating substrates are typically used for western blot, microarrays and immunohistochemistry detection and are, therefore, well known in the literature and available for use in the present assay methods.

TABLE 1

Precipitating chromogenic substrates for HRP and AP.

| Substrate | Format | Enzyme | Features | Relative sensitivity | Signal/colour |
|---|---|---|---|---|---|
| DAB | Dry powder | HRP | Can be formulated | Medium | Brown |
| Metal-enhanced DAB | 2-component reagent kit | HRP | 50× more sensitive than DAB | High | Brown/Black |
| BCIP | Dry powder | AP | Can be formulated | Medium | Blue to purple |
| NBT | Dry powder | AP | Not highly toxic | Medium | Blue to purple |
| 1-step NBT/BCIP | Single step-ready to use | AP | Low background/high sensitivity | High | Black to purple |
| 1-step NBT/BCIP + suppressor | Single step-ready to use | AP | Contains levamisole for endogenous phosphatase inhibition | high | Black to purple |
| TMB (1 component) | Single step-ready to use | HRP | Low toxicity, very high signal, ready to use | highest | Blue |

TABLE 1-continued

Precipitating chromogenic substrates for HRP and AP.

| Substrate | Format | Enzyme | Features | Relative sensitivity | Signal/colour |
|---|---|---|---|---|---|
| TMB (2 components) | 2-component reagent kit | HRP | Low toxicity, very high signal | highest | Blue |
| Precipitating TMB | Single step-ready to use | HRP | Low toxicity, very high signal, ready to use | highest | Blue |
| ELF 97 reagent | Single step-ready to use | AP | Very high signal, ready to use | highest | Yellow |
| AEC | Single step-ready to use | HRP | Low sensitivity, ready to use | low | Light brown to red |
| OPD | Dry | HRP | Can be formulated | low | Yellow/orange |

Antibodies, including antibody fragments, suitable for use in the methods described herein are known in the art. For example, the antibody or the antibody fragment may be selected from one or more of the classes IgA, IgD, IgE, IgG and IgM. In a preferred embodiment, the antibody or antibody fragment is of the IgG type. The antibody binds selectively to the target species. The antibody or antibody fragment may be derived from a mammal, including, but not limited to, a mammal selected from a human, a mouse, a rat, a rabbit, a goat, a sheep, and a horse. In an embodiment, the probe molecules comprise an antibody of the IgG type derived from a goat. The antibodies can also be created using libraries and recombinant technologies that are well established.

Figure 2:
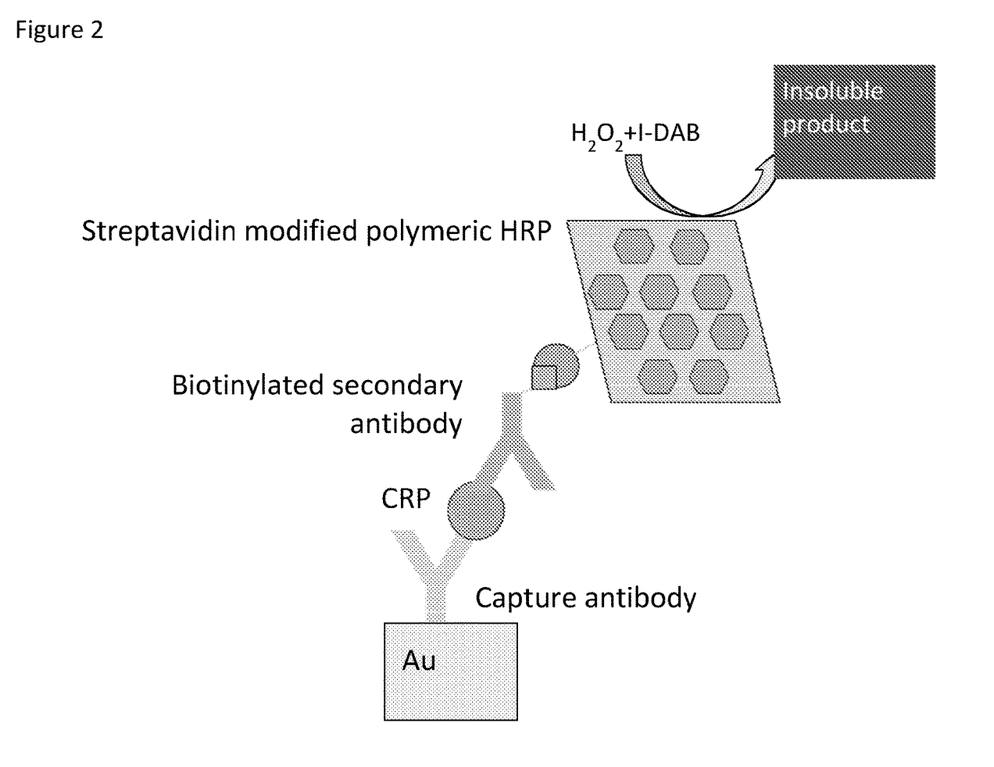
FIG. 2 provides a schematic diagram of the sandwich assay configured to detect C-reactive protein (CRP).

The target analyte may be any analyte that can be detected using an antibody or antibody fragment. A sandwich assay, as provided herein, is shown schematically in FIG. 2; in this particular configuration the secondary antibody (bearing the enzyme label) binds directly to the target analyte, as shown in FIG. 2. In other configurations binding of the secondary antibody may be indirect. In the case of indirect binding a detecting antibody may be used which binds to the target antigen and the secondary antibody (enzyme labelled) binds to the detecting antibody; this format may be particularly useful in a multiplex assay format.

Aside from the concentration of the DAB polymer substrate and incubation time, the degree of polymerisation of the DAB can also be controlled by the number of HRP enzymes present on each secondary antibody. For maximum amplification polymeric HRP (i.e. multiple HRP units on each secondary antibody) is used.

Suitable polymeric enzyme labels for antibodies are known in the literature as they are used in immunohistochemistry applications; see for example, WO2015171938 (incorporated herein by reference in its entirety). Thus, the methods provided herein may utilise any suitable polymeric enzyme label with an appropriate precipitate generating substrate. Suitable polymeric labels may include poly-HRP or streptavidin-poly-HRP conjugates. These conjugates are created by using branched polymers, such as dextran or other homo- or hetero dendrimer polymers. Suitable polymeric enzymes include Streptavidin-poly HRP 20, Streptavidin poly HRP 40, Streptavidin poly HRP 80, Antibodies (IgG) conjugated with poly HRP, Antibodies (IgG) conjugated with poly ALP (alkaline phosphatase).

Certain assay methods provided herein utilise electrical impedance spectroscopy methods to determine the presence and/or amount of insoluble precipitate on the electrode surface and thus determine the presence and/or amount of target analyte in a sample. Other electrical measurement techniques may include differential pulse voltammetry, square wave voltammetry, cyclic voltammetry, chronoamperometry, open circuit potential or chronopotentiometry.

Typically, the electrodes used in the methods provided herein comprise antibodies disposed on the planar surface of a substrate.

The substrate (surface) of the electrode may comprise any electrically conducting material. The electrode surface may comprise a metal or carbon. The metal may be a metal in elemental form or an alloy of a metal. Optionally, the whole of the electrode surface comprises a metal or carbon. The electrode surface may be comprised from transition metal. The electrode surface may comprise a transition metal selected from any of groups 9 to 11 of the Periodic Table. The surface may comprise a metal selected from, but not limited to, rhenium, iridium, palladium, platinum, copper, indium, rubidium, silver and gold. The surface may comprise a metal selected from gold, silver and platinum.

The surface may comprise a carbon-containing material, which may be selected from edge plane pyrolytic graphite, basal plane pyrolytic graphite, glassy carbon, boron doped diamond, highly ordered pyrolytic graphite, carbon powder, and carbon nanotubes.

Preferably the electrode surface can not catalyse or partake in redox chemistry or act to reduce or oxidise components of the reaction. In embodiments provided herein, the electrode surface comprises gold, for example the surface is a gold surface.

The electrode surface may be blocked using an agent to assist enzyme stability or to reduce non-specific sticking of incorrectly bound enzyme. Suitable blocking agents may include Stabilblock, Stabilzyme, Superblock or a protein such as bovine serum albumin (BSA). The blocking agent saturates the area of the electrode that has not been coated with antibodies and prevents non-specific interactions with other components of the assay (i.e secondary antibodies, antigen adsorbing on the surface, labels such as HRP of ALP). Furthermore, when using HRP and peroxide based detection systems (such as TMB or DAB) most metals will present an autocatalytic activity that will turnover the production of precipitating reagent without the presence of HRP. This is due to the fact that the metal surface can catalyse a reaction to create radicals which in turn oxidise the TMB. By carefully selecting the blocker which can cover most of the metal area it is possible to subsequently greatly attenuate this catalytic effect. Therefore the assay has much lower background even if run in a metal electrode. In addition, assays described herein rely on the deposition of either electroactive or electro-inactive precipitating reagents that are being then measured electrochemically using an array of techniques. The blocking agent plays a critical role in anchoring the precipitate that is being produced from the enzymatic reaction. There are cases, that depending on the nature of the material (i.e very flat metal surfaces), the precipitate is not stably captured on the surface and is washed away during the final wash step to terminate the reaction. Selecting the appropriate blocker for each material ensures greater and more stable deposition of the precipitating products, which leads to increased sensitivity and reduced assay error.

Suitable assay devices, impedance measuring apparatus and impedance measurement methods for use in the practice of the assay methods provided herein are known in the art, for example as described in WO2014006394 and U.S. Pat. No. 8,425,745 (incorporated herein by reference in their entirety). The assay methods provided herein may be performed such that the impedance signal is measured during the precipitation event by use of a compatible redox probe. For the DAB substrate probes are specifically chosen to have potentials below that of DAB [~200 mV vs Ag|AgCl), including ruthenium hexamine, Prussian blue, soluble derivatives of ferrocene. Alternatively, the signal is measured during the precipitation reaction non-faradaically.

The assay methods provided herein may be performed such that the elapsed time from the addition of enzyme substrate (e.g. DAB+$H_2O_2$) and either a redox probe (for Faradaic) or no redox probe (for non-Faradaic), until a particular impedance value (threshold value) is reached at a characteristic frequency is used to indirectly measure the amount of bound enzyme label and thus primary antibody/target analyte at the surface (the longer time indicates less target a).

The characteristic frequency for determining the formation of precipitate using time as an indirect signal may be determined using immittance function analysis.

The assay methods provided herein may be performed such that the signal used to directly determine the quantity of DAB precipitate formed is the current, or a function of the current, through time that is due to reduction of oxygen generated by performing chronoamperometry at a particular potential during or after the precipitation reaction.

The assay methods provided herein may be performed such that more than one redox probe is present for the impedance measurement, which may take place during or after the enzyme polymerisation reaction (following the addition of the enzyme substrate). For example, measurement in a solution of DAB+$H_2O_2$+ruthenium hexamine+Prussian blue) or as a separate solution that is added after the precipitation reaction.

The assay methods provided herein may be performed using redox probes that are specifically chosen to have varying levels of sensitivity to the insoluble precipitate (e.g. DAB) by choosing a combination of inner sphere redox probes (such as ruthenium hexamine and ferrocene carboxylic acid) and more outer sphere redox probes (such as $K_4Fe(CN)_6$, Prussian blue, oxygen), such that the linear range of sensitivity of the system is made larger.

The assay methods provided herein may be performed such that the amount of insoluble precipitate on the surface (e.g. DAB) is determined by performing direct oxidation of the precipitate (e.g. DAB) in the solution by using cyclic voltammetry and properties of this trace are used to determine the signal. Surface bound DAB makes oxidation of DAB in solution more catalytic—seen by a more negative anodic peak.

The methods provided herein allow highly sensitive EIS measurements to be performed on a single device. The primary antibody can be coated onto the electrode arrays and stored dry meaning the assay can be performed in two short steps: firstly, of the analyte and secondary antibody and, secondly, of the DAB monomer and $H_2O_2$. This process takes only minutes and can be incorporated into a cartridge with the electrochemical measurements immediately accessible with exchange of solution. For determination of unknown concentrations of antigens in solutions standard (calibration) curves can be created using known concentrations and the real values calculated. These calibration curves can be created for entire batches of electrodes. Finally, as arrays of multiple electrodes can be used simultaneously in a single device it is possible to perform biological multiplexing, i.e. measuring several analytes from a single sample. The only requirement being different primary antibodies need to be loaded on different electrodes with a single chip and either specific complimentary secondary (enzyme labelled) antibodies are used or an indirect sandwich assay is used as described above (e.g. analyte specific detecting antibodies plus enzyme labelled secondary antibodies).

The reaction may be used to determine the amount of any component of a biological sample. The biological sample can be a blood sample. The sample can be whole blood or a blood component such as serum or plasma. Any preferred biomarker can be analysed. The components detected can be antibodies or other proteins. The disease or indication being tested can be for example:

Sepsis
Autoimmune diseases
Cancer
Neurodegenerative diseases
Inflammation
Bacterial infections
Viral infections
Diabetes
Bone disease
Renal diseases
Liver-related diseases
Kidney-related Diseases

EXAMPLES

1) Example for Assay Using DAB and TMB
a) Example with DAB

In this setup, a sandwich CRP assay is performed on an electrode array. An anti-CRP antibody is physically adsorbed or chemically conjugated to the surface of the electrode. A secondary antibody that has been selected against another epitope of CRP and conjugated with an enzyme tag (e.g. HRP and ALP) is simultaneously incubated over the electrode array along with the sample, that can be either serum, plasma, urine, saliva etc. for a duration of 5 minutes. After the incubation step, a wash step is introduced to remove any unbound excess material (antibody or antigens). Then, a precipitating solution (e.g. DAB, AEC, BCIP/NBT), which is capable of creating insoluble precipitates is added to the sensor for a controlled period of time and reacts with the enzyme to produce an insulating precipitate on the electrode surface. The quantity of the precipitate (which is proportional to the amount of HRP-tagged secondary and thus proportional to the amount of antigen) can be measured electrochemically using standard faradaic impedance spectroscopy. In this, an impedance spectrum is measured in a solution containing a reversible redox probe such as ferrocene carboxylic acid, at the half-wave potential of this redox couple. By fitting the resulting spectrum to a suitable equivalent circuit, a value for the charge transfer resistance, $R_{ct}$, can be derived. The increase in the magnitude of the charge transfer resistance will be proportional to the amount of the insulating precipitate created on the surface. Alternatively, other parameters derived from the impedance response such as the change in capacitance, or the magnitude or phase at a single frequency may be used to transduce the signal.

b) Example Using TMB (Electroactive)

In this setup, a sandwich CRP assay is performed on an electrode array. An anti-CRP antibody is physically adsorbed or chemically conjugated to the surface of the electrode. A secondary antibody that has been selected against another epitope of CRP and conjugated with an enzyme tag (e.g. HRP and ALP) is simultaneously incubated over the electrode array along with the sample, that can be either serum, plasma, urine, saliva etc. for a duration of 5 minutes. After the incubation step, a wash step is introduced to remove any unbound excess material (antibody or antigens). Precipitating solution (e.g. precipitating TMB or other chromogen precipitating materials), which create insoluble precipitates are added to the sensor for a controlled period of time and react with the enzyme to produce an electroactive precipitate on the electrode surface. The quantity of the precipitate (which is proportional to the amount of HRP-tagged secondary and thus proportional to the amount of antigen) can be measured electrochemically using any of a range of techniques which include chronoamperometry, cyclic voltammetry, pulsed voltammetric methods such as DPV and SWV, and potentiometric methods such as OCP or chronopotentiometry. For example, the amount of the precipitate can be measured using DPV by scanning from low to high potential in an inert electrolyte and measuring the peak oxidative current generated as the precipitate (initially in reduced form at low potentials) is re-oxidised.

c) Example of Different Use of EIS/DPV/SWV/Chronoamperometry

The electroactive precipitate may be measured chronoamperometrically by holding a potential that causes oxidation or reduction of the precipitate and measuring the current through time. This measurement can take place during incubation of the array in the precipitating solution or after the reaction has been stopped. The current can be measured after it has reached a steady state, or at a fixed time after application of the potential. This current is proportional to the amount of enzyme at the surface and thus the concentration of antigen.

The electroactive precipitate may also be measured potentiometrically, either at open circuit (OCP) or with application of a fixed current (chronopotentiometrically). Measurement can take place during precipitation or after in a second buffer. These measurements are possible where the precipitate causes a change to the potential on the working electrode, as is the case for TMB precipitates that form on gold.

2) Correction Steps for EIS and DPV

The raw value of the charge transfer resistance, Rct, generated by fitting the impedance plot to a suitable equivalent circuit, can be taken as the signal. In general this doesn't need correction as the initial resistance (before precipitation) is a small value which can be neglected compared to the magnitude of that when the precipitate is present. For directly measured electroactive precipitates such as TMB, voltammetric measurements require subtraction of the non-specific baseline current, which can be performed post-measurement by standard numerical techniques. The peak current after this baseline subtraction can be taken as the signal.

Chemicals and reagents: Standard reagents were purchased from Fisher Scientific at standard analytical grade unless otherwise noted. PBS and carbonate buffers were made at standard concentration using the Sigma-Aldrich procedure and PBS-Tween (PBST) was made by addition of Tween surfactant (0.05%).

Electrode preparation: Gold electrodes (Eastman Au2, either bare or in array format) were cleaned by immersion in a 1% v/v solution of vol/vol Hellmanex™ III detergent and shaken gently for 30 minutes. The electrodes were the rinsed thoroughly in 18.2 MΩ water followed by UV-ozone cleaning for 20 minutes. The electrodes were immediately immersed in carbonate buffer followed by shaking for 2 minutes.

Primary antibody incubation: The cleaned electrodes were immersed in a standard solution (details) of the primary antibody (Biotechne) and incubated for 1 hour. The electrodes were then cleaned thoroughly by washing in PBST followed by immersion in a Stabilblock (Surmodics) for 30 minutes. The electrodes could then be used fresh or dried for later use.

Sandwich assay: The prepared electrodes were incubated in diluted solutions of the analyte and modified secondary antibody (Biotechne) for times between 1 and 60 minutes (with 5 being typical). This was followed by thorough washing using PBST and the addition of a solution of DAB (ImmPACT DAB, Vector labs) for between 3 and 5 minutes which forms an insoluble product via polymerisation. The electrodes were then washed thoroughly in PBS and stored in PBS until measurement.

Electrochemical measurement: Electrochemical measurements were performed in a solution of 2 mM ferrocene carboxylic acid (FcCOOH) in PBST using an Ag/AgCl reference electrode and a platinum wire counter electrode using PalmSens 4 potentiostat. A single cyclic voltammogram was performed between 0 and 0.7 V vs Ag/AgCl at 0.1 $Vs^{-1}$ followed by the electrochemical impedance spectroscopy at 0.316 V vs Ag/AgCl with an amplitude of 10 mV between 0.5 Hz and 100 kHz.

Spectra were fitted using software written in house to extract the $R_{CT}$ and the corresponding concentrations of analyte were calculated using a standard curve.

Calibration curve generation: Calibration curves were generated using pooled plasma spiked with concentrations of analyte to represent physiological concentrations.

Figure 3:
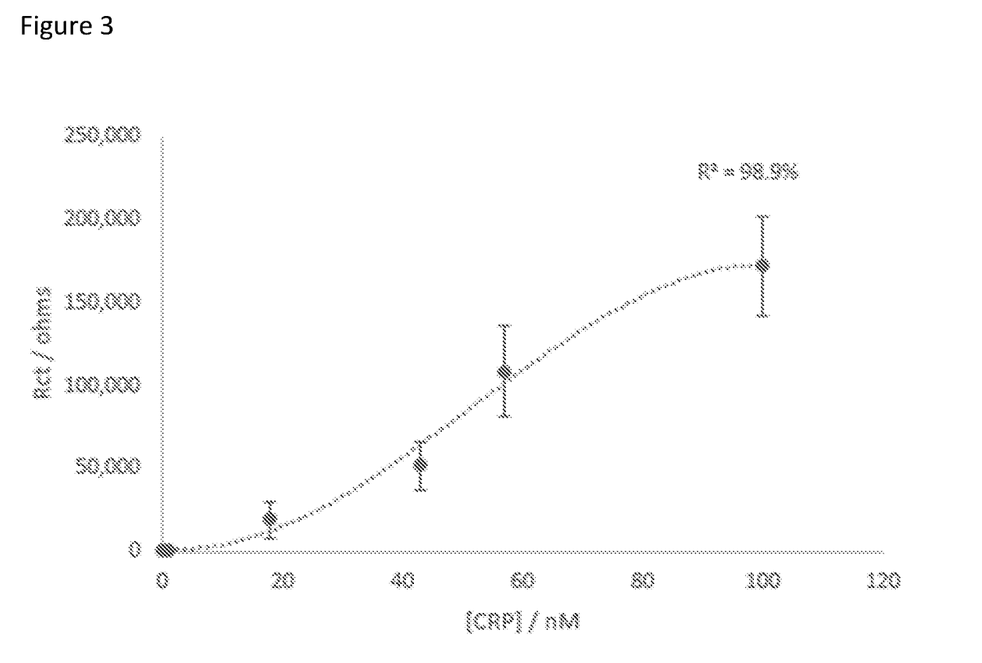
FIG. 3 shows a calibration curve for CRP obtained using 5 minute incubation time followed by 3 minutes DAB polymerisation time.
Figure 4:
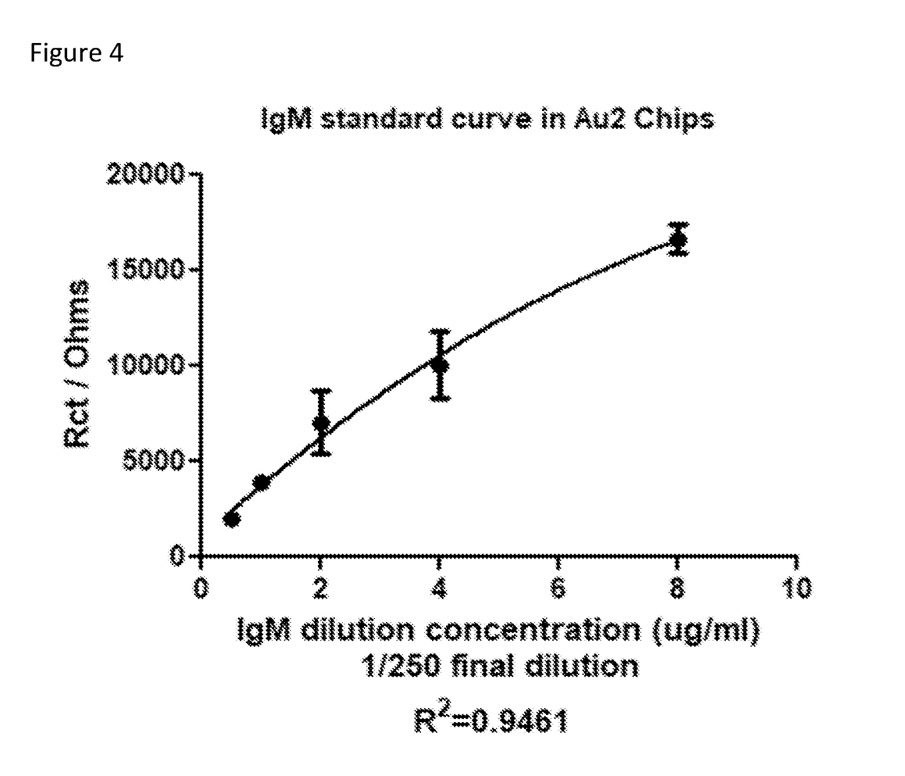
FIG. 4 shows a calibration curve for IgM using 5 minute incubation time followed by 3 minutes DAB polymerisation time.

Results:

FIGS. 3 and 4 show typical calibration curves for 2 different analytes, CRP and IgM. It is clear that this sandwich assay method coupled with EIS can be used to generate analytical curves for physiological antigens at physiologically-relevant analyte concentrations. The electrochemical measurement itself takes approximately 1 minute.

Figure 5:
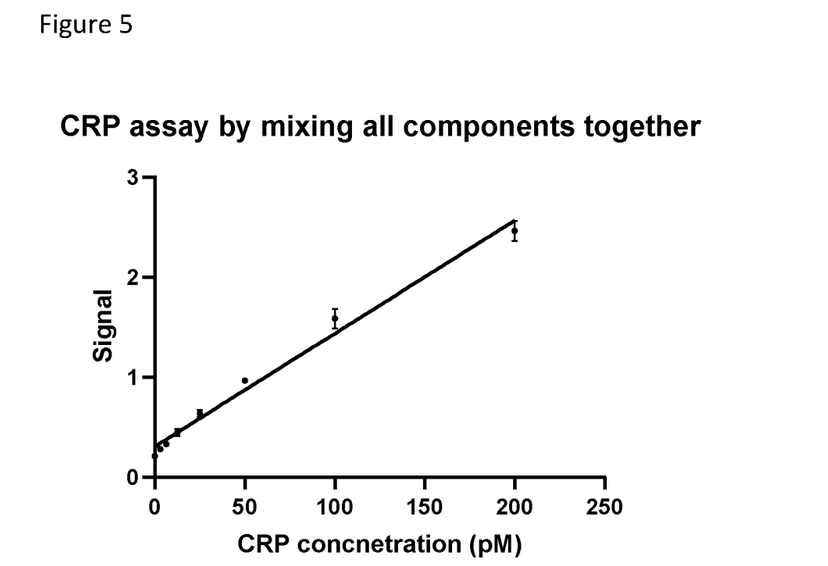
FIG. 5 shows a CRP 7-point standard curve with a 5-minute incubation for all the steps together for the secondary antibody, CRP antigen and HRP polymer.

FIG. 5 shows a CRP 7-point standard curve with a 5-minute incubation for all the steps together for the secondary antibody, CRP antigen and HRP polymer. Signal was developed for a further 3 min. N=12 runs for each point. Overall CV=6.03% for all 7 points.

Figure 6:
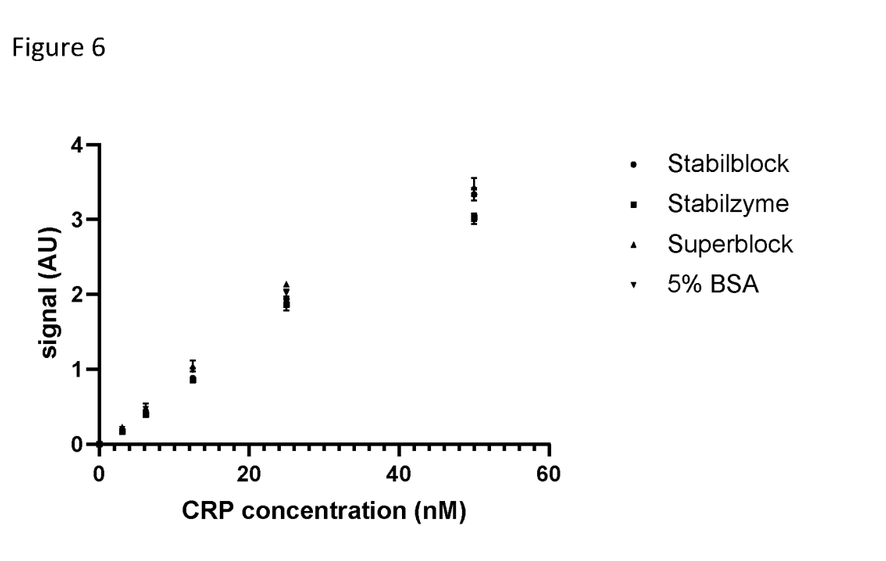
FIG. 6 shows a CRP assay consisting of a 5-point calibration curve. In this specific example different blocking formulations were utilised.

FIG. 6 shows a CRP assay consisting of a 5-point calibration curve. In this specific example different blocking formulations were utilised. These were screened from a pool of 10 different formulations. As seen, from the graph most formulations perform similarly, although Stabilzyme yields a lower signal than the other blockers. N=3 per group.

CONCLUSIONS

The enzyme boost method for electrochemical impedance-based immunoassays is capable of rapidly measuring physiological concentrations of antigens in complex media in around 10 minutes. Furthermore, it is highly suitable for use on a single fluidic device only requiring solution exchange between 3 solutions of the analyte, DAB and electrochemical measurement solution, with each step taking less than 5 minutes each.

REFERENCES

1. X. Yu, R. Lv, Z. Ma, Z. Liu, Y. Hao, Q. Lia and D. Xu, Analyst, 2006, 131, 745-750
2. Li J, Wang J, Guo X, Zheng Q, Peng J, Tang H and Yao S, Anal Chem. 2015 Aug. 4; 87 (15): 7610
3. X. Geng, F. Zhang, Q. Gao, Y. Lei, Analytical Sciences, October 2016; vol 32; 1105
4. C. Ruan, L. Yang and Y. Li, Anal. Chem., 2002, 74, 4814-4820

The invention claimed is:

1. A method for detecting a binding event between an immobilised primary antibody and a target analyte-secondary antibody-enzyme complex using an electrochemical measurement technique, the method comprising:
    incubating a target analyte, a secondary antibody and an enzyme label in a single solution;
    contacting a primary antibody immobilised on an electrode surface with the single solution of the target analyte, the secondary antibody and the enzyme label to create a sandwich complex bound to the electrode surface;
    contacting the sandwich complex with a substrate for the enzyme, wherein the substrate is converted by the enzyme into an insoluble precipitate on the electrode surface; and
    measuring an electrochemical signal during and/or after the formation of the insoluble precipitate on the electrode surface.

2. The method of claim 1, wherein the target analyte, secondary antibody and enzyme label are incubated for up to 5 minutes before contacting the primary antibody.

3. The method of claim 1 wherein the enzyme is selected from horseradish peroxidase (HRP), alkaline phosphatase, glucose oxidase and 13-galactosidase.

4. The method of claim 1, wherein the enzyme label is in a polymeric form.

5. The method of claim 1, wherein the substrate is one or more of the following; DAB, metal-enhanced DAB, AEC, BCIP, NBT, TMB, ELF or OPD.

6. The method of claim 1, wherein the primary antibody is immobilised on the electrode surface by EDC/NHS activation or passive adsorption.

7. The method of claim 1, wherein the electrochemical measurement technique is electrochemical impedance spectroscopy, differential pulse voltammetry, square wave voltammetry, cyclic voltammetry, chronoamperometry, open circuit potential or chronopotentiometry.

8. The method of claim 7, wherein the duration of the differential pulse voltammetry measurement is between 30 seconds to 2 mins.

9. The method of claim 7, wherein the duration of electrochemical impedance measurement is between 1 and 5 mins, 1 to 4 mins, 1 to 3 mins, 2 to 3 mins or, preferably, 1 to 2 mins.

10. The method of claim 9, wherein the electrochemical impedance spectroscopy measurement comprises faradaic impedance measurement.

11. The method of claim 9, wherein the electrochemical impedance spectroscopy measurement uses the elapsed time from addition of the single solution until a threshold impedance value is reached at a characteristic frequency to quantify the binding event.

12. The method of claim 11, wherein the characteristic frequency is determined using immittance function analysis.

13. The method of claim 9, wherein the electrical impedance spectroscopy measurement comprises measuring the reduction of oxygen generated by chronoamperometric measurement.

14. The method of claim 9, wherein more than one redox probe is present for the impedance measurement.

15. The method of claim 9, wherein the electrochemical impedance spectroscopy measurement is non-faradaic impedance measurement.

16. The method of claim 1, wherein the electrode is gold or carbon.

17. The method of claim 1, wherein the target is C-reactive protein (CRP) or troponin.

18. A method for detecting a binding event between an immobilised primary antibody and a CRP-secondary antibody-HRP complex using an electrochemical measurement technique, the method comprising:
    incubating a sample containing CRP, a secondary antibody and an enzyme label in a single solution, wherein the enzyme label is HRP;
    contacting a primary antibody immobilised on an electrode surface with the single solution of the target analyte, the secondary antibody and the enzyme label to create a sandwich complex bound to the electrode surface;
    contacting the sandwich complex with a substrate for the HRP, wherein the substrate is converted by the enzyme into an insoluble precipitate on the electrode surface; and
    measuring an electrochemical signal during and/or after the formation of the insoluble precipitate on the electrode surface.

* * * * *

UNITED STATES PATENT AND TRADEMARK OFFICE
CERTIFICATE OF CORRECTION

| | |
|---|---|
| PATENT NO. | : 12,168,794 B2 |
| APPLICATION NO. | : 17/281063 |
| DATED | : December 17, 2024 |
| INVENTOR(S) | : Stanislav Sokolov et al. |

It is certified that error appears in the above-identified patent and that said Letters Patent is hereby corrected as shown below:

In the Claims

Under Column no. 13, Claim 3, Line no. 41 (approx.) delete "and 13-galactosidase." and insert -- and β-galactosidase. --.

Signed and Sealed this
Eleventh Day of March, 2025

Coke Morgan Stewart
*Acting Director of the United States Patent and Trademark Office*